United States Patent
Kato et al.

(10) Patent No.: US 10,415,018 B2
(45) Date of Patent: *Sep. 17, 2019

(54) METHOD FOR SCREENING FOR PLURIPOTENT STEM CELL GROWTH-PROMOTING FACTOR

(71) Applicants: KANEKA CORPORATION, Osaka-shi, Osaka (JP); NATIONAL HOSPITAL ORGANIZATION, Tokyo (JP)

(72) Inventors: Tomohisa Kato, Takasago (JP); Yonehiro Kanemura, Osaka (JP); Tomoko Shofuda, Osaka (JP); Hayato Fukusumi, Osaka (JP)

(73) Assignees: KANEKA CORPORATION, Osaka-Shi (JP); NATIONAL HOSPITAL ORGANIZATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/053,583

(22) Filed: Aug. 2, 2018

(65) Prior Publication Data

US 2018/0355324 A1 Dec. 13, 2018

Related U.S. Application Data

(62) Division of application No. 14/900,975, filed as application No. PCT/JP2014/064764 on Jun. 3, 2014, now Pat. No. 10,066,211.

(30) Foreign Application Priority Data

Jun. 28, 2013 (JP) .................. 2013-137206

(51) Int. Cl.
*C12N 5/00* (2006.01)
*C12N 5/10* (2006.01)
*C12N 5/074* (2010.01)
*G01N 33/50* (2006.01)

(52) U.S. Cl.
CPC ....... *C12N 5/0696* (2013.01); *G01N 33/5073* (2013.01); *C12N 2500/25* (2013.01); *C12N 2500/99* (2013.01); *C12N 2501/115* (2013.01); *C12N 2501/15* (2013.01)

(58) Field of Classification Search
CPC .................................. G01N 5/0696
USPC ......................................... 435/383
See application file for complete search history.

(56) References Cited

FOREIGN PATENT DOCUMENTS

WO  WO 2012/019122 A2  2/2012

OTHER PUBLICATIONS

Akopian et al., "Comparison of defined culture systems for feeder cell free propagation of human embryonic stem cells," In Vitro Cell. Dev. Biol.—Animal (2010). vol. 46, pp. 247-258
Chen et al., "Chemically defined conditions for human iPSC derivation and culture," Nature Methods (May 2011), vol. 8, No. 5, pp. 424-429
Cheng et al., "Human Adult Marrow Cells Support Prolonged Expansion of Human Embryonic Stem Cells in Culture," Stem Cells (2003), vol. 21, pp. 131-142.
Chin et al., "Identification of proteins from feeder conditioned medium that support human embryonic stem cells," Journal of Biotechnology (2007), vol. 130, No. 3, pp. 320-328.
Extended European Search Report issued in Application No. 14818252. 0, dated Oct. 20, 2016.
Fukusumi, H. and Y. Kanemura, "Development of feeder cells free culture system of human ES/iPS cells," Journal of Clinical and Experimental Medicine (Dec. 31, 2011), vol. 239, No. 14, pp. 1338-1344.
Furue et al., "Herapin promotes the growth of human embryonic stem cells in a define serum-free medium", Proceedings of the National Academy of Sciences, vol. 105, No. 36, (Sep. 9, 2008), pp. 13409-13414.
Hovatta et al., "A culture system using human foreskin fibroblasts as feeder cells allows production of human embryonic stem cells," Human Reproduction (2003), vol. 18, No. 7, pp. 1404-1409.
Lim et al., "Proteome analysis of conditioned medium from mouse embryonic fibroblast feeder layers which support the growth of human embryonic stem cells," Proteomics, vol. 2, No. 9, (Sep. 1, 2002), pp. 1187-1203.
Richards et al., "Comparative Evaluation of Various Human Feeders for Prolonged Undifferentiated Growth of Human Embryonic Stem Cells," Stem Cells (2003), vol. 21, pp. 546-556.
Richards et al., "Human feeders support prolonged undifferentiated growth of human inner cell masses and ebryonic stem cells," Nature Biotechnology (Sep. 2002), vol. 20, pp. 933-936.
Yue et al., "Feeder Cells Support the Culture of Induced Pluripotent Stem Cells Even after Chemical Fixation," PLoS ONE (Mar. 2012), vol. 7, No. 3, e32707 (9 pages).

*Primary Examiner* — Valarie E Bertoglio
(74) *Attorney, Agent, or Firm* — Birch, Stewart, Kolasch & Birch, LLP

(57) ABSTRACT

This invention relates to a method for screening for a growth-promoting factor for pluripotent stem cells with a conditioned medium which is generated by culturing feeder cells in a serum-free medium that contains L-ascorbic acid, insulin, transferrin, selenium, and sodium bicarbonate and does not contain a serum nor serum replacement; a method for growing pluripotent stem cells via feeder-free culture using the conditioned medium; and a method for growing pluripotent stem cells by carrying out feeder-free culture of pluripotent stem cells cultured in advance on feeder cells in the serum-free medium.

10 Claims, 5 Drawing Sheets

Fig. 3

| Culture substrate | Medium conditioning with MEF | Average split ratio | Final cell count | Relative ratio (growth capacity) |
|---|---|---|---|---|
| PCM-DM | Unconditioned | 1.5 | $6 \times 10^3$ | 1 |
| PCM-DM | Conditioned | 2.5 | $1.9 \times 10^5$ | 288 |
| Matrigel | Unconditioned | 1.5 | $4.5 \times 10^3$ | 1 |
| Matrigel | Conditioned | 2.25 | $2.6 \times 10^5$ | 264 |

METHOD FOR SCREENING FOR PLURIPOTENT STEM CELL GROWTH-PROMOTING FACTOR

CROSS-REFERENCE TO RELATED APPLICATIONS

This application is a Divisional of U.S. application Ser. No. 14/900,975 filed Dec. 22, 2015, now U.S. Pat. No. 10,066,211, which is a National Phase of PCT International Application No. PCT/JP2014/064764 filed on Jun. 3, 2014, which claims priority under 35 U.S.C. § 119(a) to Application No. 2013-137206, filed in Japan on Jun. 28, 2013, all of which are hereby expressly incorporated by reference into the present application

TECHNICAL FIELD

The present invention relates to a technique of feeder-free, serum-free cell culture with high efficiency and a screening method based on such culture technique.

BACKGROUND ART

Recent research on human pluripotent stem cells such as human ES cells (hESCs) and human iPS cells (hiPSCs) provides an increased potential for practical applications of regenerative medicine. Since such cells have an unlimited proliferative capacity and a differentiation capability into various cells, regenerative medicine using pluripotent stem cells is expected to fundamentally change methods for treatment of refractory diseases, lifestyle-related diseases, and other diseases. Recent techniques have already enabled the induction of differentiation of pluripotent stem cells in vitro into various cells, including nerve cells, cardiac muscle cells, blood cells, and retinal cells.

Human pluripotent stem cells, such as hESC and hiPSC, have been conventionally cultured primarily on feeder cell layers using mouse embryonic fibroblasts (MEFs). Feeder cells supply growth factors that are useful for maintenance culture of human pluripotent stem cells to stem cells. The activity to enable maintenance culture of human pluripotent stem cells has been found in various human cell types, in addition to MEFs (Hovatta O. et al., Hum. Reprod., (2003) 18, pp. 1404-1409; Richards M. et al., Nat. Biotechnol., (2002) 20, pp. 933-936; Cheng L. et al., Stem Cells, (2003) 21, pp. 131-142; and Richards M. et al., Stem Cells, (2003) 21, pp. 546-556). However, in conventional techniques, the preparation of feeder cells at the time of culture has been laborious, and there is a risk of contamination of feeder cells in stem cells. Therefore, the development of alternative safer techniques has been needed.

As a pluripotent stem cell culture technique without using MEFs, a method involving the use of a MEF-preliminarily conditioned medium (i.e., MEF-CM) from a medium supplemented with a serum such as FBS or a serum replacement and a method with the use of chemically fixed MEFs (Yue X-S. et al., PLoS. ONE, (2012) 7, e32707) are known. In addition, a method involving the use of various human cells (e.g., fibroblasts, placental cells, bone marrow cells, and endometrial cells) as living feeder cells without using xenogeneic cells has been reported (Hayato Fukusumi and Yonehiro Kanemura, Development of Feeder-free Cell Culture Technique of Human ES/iPS Cells, Journal of Clinical and Experimental Medicine, (2011) 239, pp. 1338-1344). In these methods, a medium supplemented with bovine serum or KNOCKOUT™ SR (Knockout Serum Replacement, which is an additive used as a serum replacement for enabling culture of ES/iPS cells) is used in order to culture human pluripotent stem cells. However, many of the additive components comprise proteins extracted from bovine serum. Accordingly, infectious diseases such as bovine spongiform encephalopathy (BSE) and viral contamination of cells become issues of concern. While human serum is used on some occasions, human serum is not suitable for practical use because of restrictions in use thereof or quantitative limitations.

In addition, the development of complete synthetic medium (chemically defined medium) for culture without MEFs has been advanced (Akopian V. et al., In Vitro Cell Dev. Biol. Anim., (2010) 46, pp. 247-258; and Chen G. et al., Nat. Methods, (2011) 8, pp. 424-429). MEF secretory products are analyzed for functional proteins (Chin A. C. et al., J. Biotechnol., (2007) 130, pp. 320-328). However, it remains difficult to stably culture human pluripotent stem cells in feeder-free, serum-free culture, and development of a technique that enables satisfactory growth has been awaited.

SUMMARY OF THE INVENTION

Problem to be Solved by the Invention

It is an object of the present invention to provide a technique of feeder-free, serum-free cell culture with high efficiency. It is another object of the present invention to provide a method of screening for growth-promoting factors based on such culture technique.

Means for Solving the Problem

The present inventors have conducted concentrated studies in order to attain the above objects. As a result, they discovered that conditioning of serum-free medium, which can be used for pluripotent stem cell culture, with feeder cells in advance would enable preparation of a medium that would enable the stable culture of pluripotent stem cells and improve the growth capacity without co-culture with feeder cells. They also discovered a technique that could be used to efficiently identify pluripotent stem cell growth-promoting factors via screening of such prepared medium. This has led to the completion of the present invention.

In addition, the present inventors discovered that the growth capacity of pluripotent stem cells could further be improved by on-feeder culture of pluripotent stem cells in a serum-free medium containing particular components, followed by feeder-free culture.

Specifically, the present invention includes the following.
[1] A method for screening for a growth-promoting factor for pluripotent stem cells comprising:
  a) culturing feeder cells in a serum-free medium that contains L-ascorbic acid, insulin, transferrin, selenium, and sodium bicarbonate and does not contain a serum nor serum replacement to generate a conditioned medium and recovering the conditioned medium; and
  b) detecting a growth-promoting factor for pluripotent stem cells in the recovered conditioned medium.

In a preferred embodiment of the screening method, the serum-free medium may be DMEM/F12 medium containing L-ascorbic acid, insulin, transferrin, selenium, and sodium bicarbonate.

In an embodiment of the screening method, the culturing of the feeder cells is preferably carried out with the addition of a growth factor to the serum-free medium. The growth factor to be added in the screening method is preferably FGF2 and/or TGF-β1.

In the screening method, the feeder cells can be mouse embryonic fibroblasts.

In the screening method, the pluripotent stem cells are preferably ES cells or iPS cells.

[2] A method for preparing a medium for culturing pluripotent stem cells comprising culturing feeder cells in a serum-free medium that contains L-ascorbic acid, insulin, transferrin, selenium, and sodium bicarbonate and does not contain a serum nor serum replacement to generate a conditioned medium and recovering the conditioned medium.

In a preferred embodiment of the preparation method, the serum-free medium may be DMEM/F12 medium containing L-ascorbic acid, insulin, transferrin, selenium, and sodium bicarbonate.

In an embodiment of the preparation method, the culturing of the feeder cells is preferably carried out with the addition of a growth factor to the serum-free medium. The growth factor to be added in the preparation method is preferably FGF2 and/or TGF-β1.

In the preparation method, the feeder cells may be mouse embryonic fibroblasts.

In the preparation method, the pluripotent stem cells are preferably ES cells or iPS cells.

[3] A conditioned medium for culturing pluripotent stem cells, which is prepared by the method according to [2] above.

[4] A method for growing pluripotent stem cells comprising carrying out feeder-free culture of pluripotent stem cells in a conditioned medium which is generated by culturing feeder cells in a serum-free medium that contains L-ascorbic acid, insulin, transferrin, selenium, and sodium bicarbonate and does not contain a serum nor serum replacement.

In a preferred embodiment of the growth method, the serum-free medium may be DMEM/F12 medium containing L-ascorbic acid, insulin, transferrin, selenium, and sodium bicarbonate.

In an embodiment of the growth method, the culturing of the feeder cells is preferably carried out with the addition of a growth factor to the serum-free medium. In another embodiment, it is preferred that the culturing of the feeder cells be carried out without the addition of growth factors to the serum-free medium and feeder-free culture of pluripotent stem cells be carried out with the addition of a growth factor to the conditioned medium. The growth factor to be added in the growth method is preferably FGF2 and/or TGF-β1.

In the growth method, the feeder cells may be mouse embryonic fibroblasts.

In the growth method, the pluripotent stem cells are preferably ES cells or iPS cells.

[5] A method for growing pluripotent stem cells comprising transferring pluripotent stem cells cultured on feeder cells using a serum-free medium that contains L-ascorbic acid, insulin, transferrin, selenium, and sodium bicarbonate and does not contain a serum nor serum replacement, to a culture in the absence of feeder cells, and carrying out feeder-free culture of the pluripotent stem cells.

In a preferred embodiment of such method, the serum-free medium does not preferably contain albumin.

This description includes the disclosure in Japanese Patent Application No. 2013-137206 to which the present application claims priority.

Effects of the Invention

According to the present invention, the growth capacity of pluripotent stem cells in feeder-free culture can be improved with a serum-free medium, which does not contain a serum nor serum replacement. In addition, according to the present invention, a conditioned medium that enables screening for factors that promote the undifferentiated growth of pluripotent stem cells in feeder-free culture can be prepared.

BRIEF DESCRIPTION OF THE DRAWINGS

FIG. 3 presents a table showing the results of comparison of the human iPS cell growth capacity in culture using MEF-conditioned serum-free medium or unconditioned serum-free medium.

In FIGS. 5A-5J, the extent of the growth is indicated by the symbol "−" (not grown) or the numbers of "+".

EMBODIMENTS FOR CARRYING OUT THE INVENTION

Figure 1:
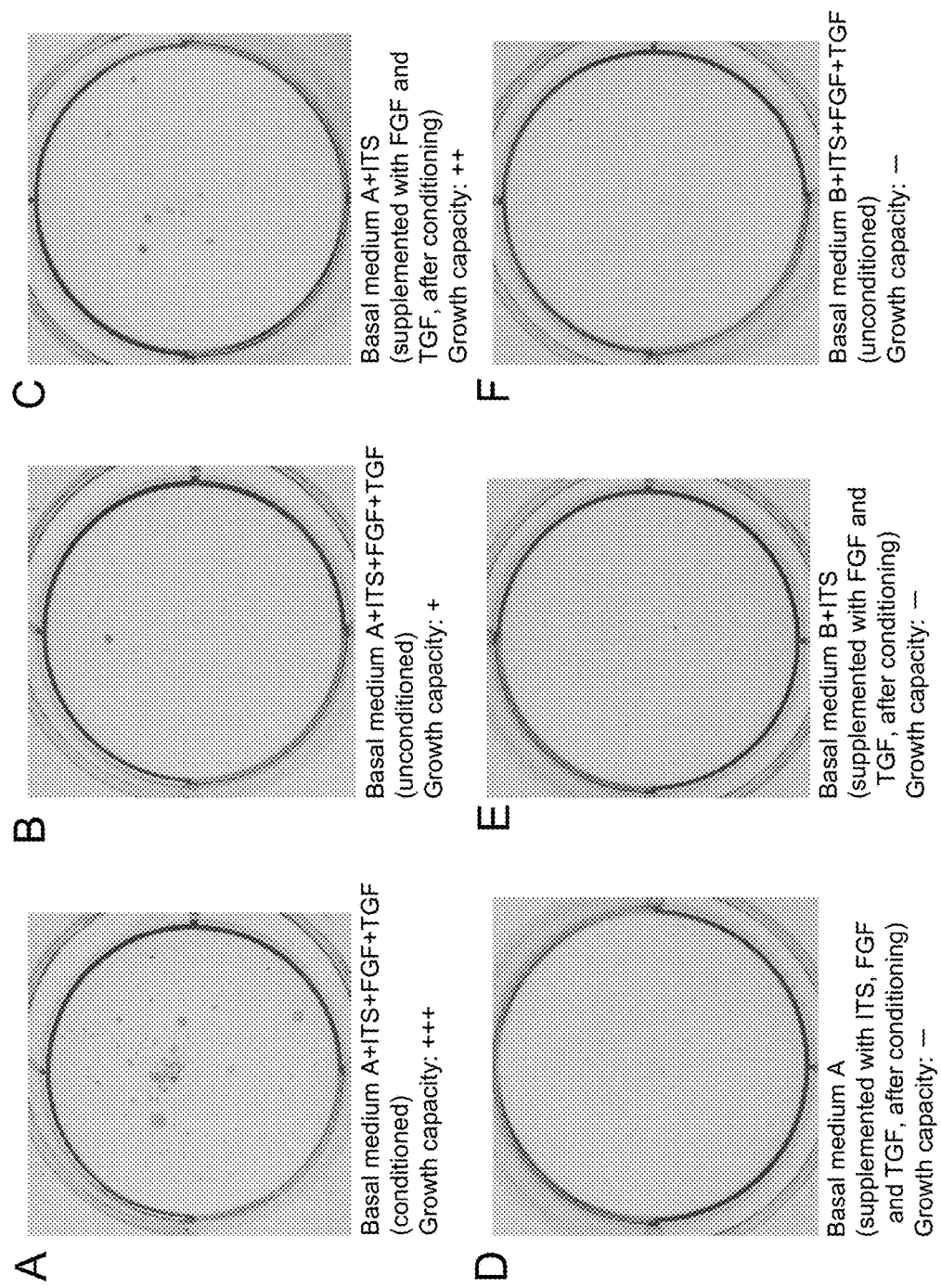
FIG. 1 presents photographs showing the effects of serum-free MEF-conditioned medium on the growth capacity of iPS cells in feeder-free culture. A: the growth capacity (+++) in a conditioned medium prepared from a basal medium (serum-free medium) A+ITS+FGF2+TGF-β1; B: the growth capacity (+) in a basal medium (serum-free medium) A+ITS+FGF2+TGF-β1 (unconditioned); C: the growth capacity (++) in a conditioned medium (supplemented with FGF2+TGF-β1, after conditioning) prepared from a basal medium (serum-free medium) A+ITS; D: the growth capacity (−) in a conditioned medium (supplemented with ITS+FGF2+TGF-β1, after conditioning) prepared from a basal medium (serum-free medium) A; E: the growth capacity (−) in a conditioned medium (supplemented with FGF2+TGF-β1, after conditioning) prepared from a basal medium (serum-free medium) B+ITS; and F: the growth capacity (−) in a basal medium (serum-free medium) B+ITS+FGF2+TGF-β1 (unconditioned).

Hereafter, the present invention is described in greater detail.

The present invention relates to a method of preparing a medium suitable for growing pluripotent stem cells in feeder-free culture, via conditioning a serum-free medium with feeder cells.

The term "pluripotent stem cell" used in the context of the present invention refers to a cell having multipotency (pluripotency) that is capable of differentiating into any types of cells constituting an living body and capable of unlimitedly proliferating (growing) while maintaining pluripotency via in vitro culture. Specific examples of pluripotent stem cells to be grown in the present invention include, but are not limited to, embryonic stem cells (ES cells), fetal primordial germ cell-derived pluripotent stem cells (EG cells; Shamblott M. J. et al., Proc. Natl. Acad. Sci., U.S.A., (1998) 95, pp. 13726-13731), testis-derived pluripotent stem cells (GS cells; Conrad S., Nature, (2008) 456, pp. 344-349), and somatic cell-derived induced pluripotent stem cells (iPS cells). The pluripotent stem cells to be grown in the present invention are particularly preferably are ES cells or iPS cells. ES cells are cultured cells that are derived from undifferentiated cells obtained from inner cell mass in early embryos called blastocysts. iPS cells are cultured cells that are prepared by introducing reprogramming factors into somatic cells to reprogram the somatic cells to an undifferentiated state, thereby imparting pluripotency thereto. As the reprogramming factors, Oct family genes (e.g., Oct3/4), Klf family genes (e.g., Klf4), Myc family genes (e.g., c-Myc), and/or Sox family genes (e.g., Sox2) may be used. Pluripotent stem cells may be derived from any animal species. For example, pluripotent stem cells may be derived from mammalian animals, including rodents such as mice, rats, and hamsters, primates such as humans, gorillas, and chimpanzees, and livestock or pet animals such as dogs, cats, rabbits, bovines, horses, sheep, or goats; and particularly preferably be human-derived pluripotent stem cells. Pluripotent stem cells, including ES cells and iPS cells, may be commercially available or provided cells, or newly established cells. Alternatively, stimulus-triggered acquisition of pluripotency (STAP) cells may be used as pluripotent stem cells. STAP cells are pluripotent cells prepared via application of strong external stimuli (stress) to animal cells (Nature, 505, 641-647, (2014)).

In the present invention, a serum-free medium that contains L-ascorbic acid, insulin, transferrin, selenium, and sodium bicarbonate but does not contain a serum nor serum replacement is to be subjected to conditioning. The term "serum" used in the present invention refers to a serum derived from any animal (e.g., human, bovine, horse, or goat). The term "serum replacement" refers to a reagent for maintenance of the undifferentiated state of cells and culture thereof as an alternative to a serum (e.g., FBS) in ES or iPS cell culture. Examples of serum replacement include KNOCKOUT™ SR (KnockOut™ Serum Replacement or KSR; Gibco), StemSure® Serum Replacement (SSR; Wako Pure Chemical Industries, Ltd.), and N-2 Supplement (Wako Pure Chemical Industries, Ltd.). The serum-free medium can be prepared using any liquid medium for animal cell culture that does not contain a serum nor serum replacement as a basal medium. Examples of basal media that can be used include, but are not particularly limited to, BME medium, BGJb medium, CMRL1066 medium, Glasgow MEM medium, Improved MEM Zinc Option Medium, Iscove's Modified Dulbecco's Medium (IMDM), Medium 199, Eagle MEM medium, αMEM medium, Dulbecco's Modified Eagle's Medium (DMEM), Ham's F10 medium, Ham's F12 medium, RPMI 1640 medium, Fischer's medium, and a mixture of any combination of these media (e.g., DMEM/F12 medium (Dulbecco's Modified Eagle's Medium/Nutrient Mixture F-12 Ham)). When a serum-free medium is to be prepared with such basal medium, the basal medium can be supplemented with L-ascorbic acid, insulin, transferrin, selenium, and sodium bicarbonate.

Alternatively, a serum-free medium can be prepared with a liquid medium that does not contain a serum nor serum replacement, which has been supplemented with at least one of L-ascorbic acid, insulin, transferrin, selenium, and sodium bicarbonate in advance. In that case, components that are not contained in the prepared medium from among L-ascorbic acid, insulin, transferrin, selenium, and sodium bicarbonate may be added to the medium, to prepare a serum-free medium. Alternatively, L-ascorbic acid, insulin, transferrin, selenium, and sodium bicarbonate (which although include a component also contained in the above prepared medium) may be added to the medium to prepare a serum-free medium. For example, a medium that is free from serum-derived components and supplemented with insulin and transferrin, including CHO-S-SFM II (Gibco BRL), Hybridoma-SFM (Gibco BRL), eRDF Dry Powdered Media (Gibco BRL), UltraCULTURE™ (BioWhittaker), UltraDOMA™ (BioWhittaker), UltraCHO™ (BioWhittaker), and UltraMDCK™ (BioWhittaker), can be used. Also, STEMPRO® hESC SFM (Life Technologies), mTeSR1 (Veritas), and TeSR2 (Veritas) can be preferably used. Essential 8™ medium (Life Technologies) with very limited protein components can also be preferably used.

A preferred example of the above-mentioned serum-free medium is DMEM/F12 medium with L-ascorbic acid, insulin, transferrin, selenium, and sodium bicarbonate.

A medium to be used for the preparation of a serum-free medium in the present invention may contain fatty acid, a collagen precursor, trace elements, 2-mercaptoethanol, 3'-thiol glycerol, or equivalents of any thereof. However, the content of protein components other than growth factors is preferably as low as possible. In one embodiment of the present invention, the serum-free medium preferably does not contain albumin. This is because, while albumin is often added to a serum-free medium, it can cause significant lot-to-lot quality variations, disadvantageously. In one embodiment of the present invention, the composition of a medium to be used for the preparation of a serum-free medium is preferably known. When screening for growth-promoting factors for pluripotent stem cells from a conditioned medium, for example, it is preferred that the medium composition be known.

When preparing a serum-free medium, L-ascorbic acid, insulin, transferrin, selenium, and sodium bicarbonate can be added in any form of a solution, derivative, salt, reagent mixture or the like, to a medium for animal cell culture. For example, L-ascorbic acid may be added to a medium in the form of a derivative such as ascorbyl-2-phosphate magnesium. Selenium may be added to a medium in the form of selenite salt (e.g., sodium selenite). Insulin and transferrin may be separated from tissues, sera or the like of animals (preferably humans, mice, rats, bovines, horses, or goats) and thus naturally occurring, or insulin and transferrin may be genetically engineered recombinant proteins. Insulin, transferrin, and selenium may be added to a medium in the form of the reagent ITS (insulin-transferrin-selenium). ITS is an additive for cell growth promotion that contains insulin, transferrin, and sodium selenite.

A serum-free medium to be conditioned in the present invention may contain fatty acid or lipid, amino acid (e.g., a nonessential amino acid), vitamin, growth factor, cytokine, antioxidant, 2-mercaptoethanol, pyruvic acid, buffer, inorganic salt or the like. When the serum-free medium contains 2-mercaptoethanol, for example, the concentration is not limited, provided that the medium is suitable for stem cell culture at such concentration, but may be approximately 0.05 to 1.0 mM, and preferably about 0.1 to 0.5 mM, for example.

In the present invention, the medium is conditioned by culturing feeder cells in the above-mentioned serum-free medium. Preferably, feeder cells are first treated with mitomycin or γ-ray irradiation to inactivate mitosis, and then used for conditioning. Feeder cells used in the present invention are cells available for pluripotent stem cell culture on feeder cell layers (on-feeder culture). Feeder cells may be fibroblasts, placental cells, bone marrow cells, endometrial cells or other cells derived from embryos or tissues of mammalian animals such as humans, mice, rats, or bovines. Specific examples of feeder cells include, but are not limited to, mouse embryonic fibroblasts (i.e., MEFs and STO cell line) and derivative cell lines of STO cells (e.g., SNL cells into which neomycin-resistant gene expression vector and LIF expression vector are stably introduced).

A serum-free medium to be subjected to conditioning with feeder cells may or may not contain growth factors. Regardless of whether or not the serum-free medium contains growth factors, it is not necessarily have to add a growth factor to the serum-free medium during conditioning. However, when the serum-free medium does not contain growth factors, it is preferred that the serum-free medium be preferably supplemented with a growth factor and subjected to conditioning. The serum-free medium preferably contains as a growth factor, but not limited to, at least one selected from the group consisting of FGF2 (basic fibroblast growth factor), TGF-β1 (transforming growth factor-β1), MCP-1, IL-6, PAI, PEDF, IGFBP-2, LIF, and IGFBP-7; and for example, FGF2 and/or TGF-β1. FGF2 and TGF-β1 are particularly preferred growth factors.

Conditioning of a medium with feeder cells can be carried out by culturing feeder cells for growth, exchanging the medium in the culture vessel with the above-mentioned serum-free medium, and culturing the feeder cells therein. Culturing of feeder cells can be carried out by a conventional technique. Culture for conditioning in the serum-free medium can be carried out at 4° C. to 45° C. (e.g., 25° C. to 40° C.) for 1 to 72 hours (e.g., 8 to 36 hours). The culture is also preferably carried out at 4% to 10% $CO_2$ (e.g., 5% $CO_2$).

A culture vessel is not particularly limited, provided that it can be used for cell culture. Examples thereof include flasks, tissue culture flasks, dishes, Petri dishes, culture dishes, multi-dishes, microplates, micro-well plates, multi-plates, multi-well plates, chamber slides, plates, tubes, trays, culture bags, roller bottles, and hollow fiber culture vessels.

In the manner described above, feeder cells can be cultured in a serum-free medium to allow feeder cells to secrete growth-promoting factors and the like into the medium, thereby conditioning the serum-free medium. The resulting conditioned medium can be separated and recovered from feeder cells by conventional techniques. The recovering of the conditioned medium may be conducted by separating a liquid medium from feeder cells via filtration and/or centrifugation, for example, via centrifugation at 1,000 rpm for 5 minutes, and recovering the separated liquid medium. After the recovering of the conditioned medium, conditioning culture in a serum-free medium may be carried out repeatedly (e.g., 2 to 10 times).

As a specific example of the procedure of preparation of the conditioned medium, the conditioned medium can be prepared by culturing monolayer MEFs to confluence, treating the cultured cells with 10 μg/ml mitomycin C, detaching the cells with a cell detaching solution such as Trypsin-EDTA, seeding the recovered MEFs in a culture dish at a cell density of 3 to $5 \times 10^5$ cells per 60-mm dish, culturing for 1 to 2 days, exchanging the medium in the culture dish with the above-mentioned serum-free medium, and recovering a liquid medium therefrom every 24 hours.

The resulting conditioned medium can be suitably used as a medium for pluripotent stem cell culture, and particularly preferably used for feeder-free, serum-free, and serum replacement-free culture. In the present invention, the expression "feeder-free, serum-free and serum replacement-free culture" refers to culture which is conducted without feeder cell layers (i.e., feeder-free culture) and conducted in a medium that does not contain a serum nor serum replacement. When growth factors or medium components used in a medium do not contain xenogeneic components for the pluripotent stem cells, such a medium can be particularly preferably used as a xenogeneic component-free medium (i.e., xeno-free medium). The present invention also relates to such method of preparation of a conditioned medium for pluripotent stem cell culture and a conditioned medium for pluripotent stem cell culture obtainable by such method.

According to the present invention, the conditioned medium thus prepared may be used to conduct feeder-free culture of pluripotent stem cells. With the use of the conditioned medium, the growth capacity of pluripotent stem cells in feeder-free culture can be remarkably improved. That is, the present invention relates to a method for growing pluripotent stem cells comprising carrying out feeder-free culture of pluripotent stem cells in the above-mentioned conditioned medium.

Pluripotent stem cells to be cultured in the conditioned medium can be subjected to maintenance culture in advance by conventional techniques. Preferably, the pluripotent stem cells that had been subjected to maintenance culture are detached from the culture vessel with a detaching solution such as a collagenase solution, and the cells are recovered following forming small masses of approximately several dozen cells, e.g., approximately 20 to 50 cells. When feeder cells are used in maintenance culture, it is preferred that feeder cells be removed from the recovered pluripotent stem cells by a conventional technique. When maintenance culture is carried out using MEFs as feeder cells, for example, MEFs can be removed by incubating the recovered pluripotent stem cells in a gelatin-coated culture vessel to allow MEFs to adhere to the culture vessel, and collecting the pluripotent stem cells suspended in the medium.

The thus-prepared pluripotent stem cells are preferably seeded in a culture vessel coated with a culture substrate serving as a scaffold for cells. The culture vessel described in connection with the preparation of the conditioned medium can be also used herein. A culture substrate is not particularly limited, provided that it can be used for cell culture. Examples of culture substrate include gelatin, Matrigel® produced from Engelbreth-Holm-Swarm (EHS) mouse sarcoma, laminin (e.g., laminin-511, laminin-111, and laminin-332), fibronectin, vitronectin, collagen, E-cadherin, synthetic peptides, synthetic polymers, and extracellular matrices derived from MEF, human serum, or decidua-derived mesenchymal cells (PCM-CM). An example of synthetic polymers that can be used as a culture substrate is hydrogel, e.g., temperature-sensitive hydrogel comprising 2-(diethylamino)ethyl acrylate as a backbone (Zhang et al., Nature Communications, 2013, 4, article number: 1335). A culture vessel can be coated with such culture substrate by a conventional technique that is well known to a person skilled in the art. For example, the culture vessel can be coated by introducing a culture substrate solution (e.g., a vitronectin solution) into a culture vessel, and incubating for a given period of time (e.g., 1 hour).

Pluripotent stem cells can be cultured in the conditioned medium preferably at 20° C. to 40° C. (e.g., 35° C. to 40° C.) for 1 hour to 7 days (e.g., 1 to 24 hours), although the culture conditions are not limited thereto. Pluripotent stem cells can be preferably cultured in the conditioned medium at 4% to 10% $CO_2$ (e.g., 5% $CO_2$). Culturing of pluripotent stem cells may involve a passage culture.

The growth capacity of the pluripotent stem cells thus cultured is significantly improved, in comparison with the growth capacity attained with the use of an unconditioned medium. In a preferred embodiment, the number of the pluripotent stem cells grown in the conditioned medium increases preferably 10 times or more, more preferably 100 times or more, and further preferably 200 times or more, e.g., 250 to 300 times, compared with the number of cells grown in an unconditioned medium. The increase of the number of cells can be assessed with reference to, for example, the number of cells counted after the fifth passage. In addition, the pluripotent stem cells cultured in the conditioned medium can maintain the undifferentiated state. The undifferentiated state of the pluripotent stem cells can be verified on the basis of expression of an undifferentiation marker (e.g., genes or proteins of SSEA3, SSEA4, Tra1-60, Tra1-81, Oct4, NANOG, SOX2 or the like).

The conditioned medium thus prepared contains a substance capable of promoting the growth of pluripotent stem cells in the undifferentiated state (i.e., growth-promoting factors for pluripotent stem cells), which was secreted from feeder cells such as MEFs. According to the present invention, therefore, the conditioned medium can further be subjected to screening, in order to identify such growth-promoting factors. In the screening, a pluripotent stem cell growth-promoting factor may be detected in the conditioned medium, thereby identifying a growth-promoting factor. Thus, the present invention also provides a method for screening for a growth-promoting factor for pluripotent stem cells comprising recovering the conditioned medium thus generated and detecting a pluripotent stem cell growth-promoting factor contained in the recovered conditioned medium. The growth-promoting factors for pluripotent stem cells may be proteins or nucleic acids (e.g., RNA), amino acids, peptides, and sugar chains, or low-molecular-weight compounds such as metabolites.

In the screening method of the present invention, it is preferred that the recovered conditioned medium be separated and/or purified by any suitable techniques, followed by identifying a growth-promoting factor. For example, separation and/or purification and identification of growth-promoting factors can be carried out using electrophoresis such as two-dimensional electrophoresis, isoelectric electrophoresis, or SDS-PAGE, chromatography techniques such as high-performance liquid chromatography (HPLC), ion-exchange chromatography, or affinity chromatography, or mass spectrometry such as matrix-assisted laser desorption/ionization time-of-flight mass spectrometry (MALDI/TOFMS) or liquid chromatography/tandem mass spectrometry (LC-MS/MS). The results of the analysis of components in the conditioned medium are compared with the results of the analysis of medium components in the serum-free medium before conditioning, and the components that are differentially contained in the conditioned medium can be detected as candidates for the growth-promoting factors for pluripotent stem cells. Thus, for this purpose of screening, it is preferred that all components of the serum-free medium used for conditioning be known.

For detecting pluripotent stem cell growth-promoting factors contained in the conditioned medium, a component separated or purified or identified from the conditioned medium (in particular, a candidate component for the growth-promoting factors for pluripotent stem cells) may be added to a pluripotent stem cell culture system using a medium for pluripotent stem cell culture, and culture be then conducted. The growth capacity (the capacity of the undifferentiated growth, in particular) of the pluripotent stem cells in the culture system may be examined and compared with a control, i.e., a culture system to which the same component has not been added, in order to determine whether or not the growth capacity is enhanced. If the growth capacity (the number of grown cells) is enhanced, for example, by 10 times or more, and preferably 100 times more, the component is revealed to be a growth-promoting factor for pluripotent stem cells. The screening method of the present invention may comprise such a step of detecting the pluripotent stem cell growth promoting activity of a component in the conditioned medium. The promotion of the growth of the pluripotent stem cells in an undifferentiated state (i.e., undifferentiated growth) can be determined by further verifying the maintenance of the expression level of an undifferentiation marker (e.g., genes or proteins of SSEA3, SSEA4, Tra1-60, Tra1-81, Oct4, NANOG, SOX2 or the like).

The growth-promoting factors for pluripotent stem cells obtained by the screening method of the present invention can be added to a culture system of pluripotent stem cells to promote undifferentiated growth of the pluripotent stem cells.

The present invention also provides a method for growing pluripotent stem cells comprising transferring pluripotent stem cells cultured on feeder cells using a serum-free medium that can be used for pluripotent stem cell culture, to a culture in the absence of feeder cells and carrying out feeder-free culture of the pluripotent stem cells. In one particularly preferred embodiment of the method for growing pluripotent stem cells, pluripotent stem cells cultured on feeder cells using a serum-free medium that contains L-ascorbic acid, insulin, transferrin, selenium, and sodium bicarbonate but does not contain a serum nor serum replacement, are transferred to a culture in the absence of feeder cells and subjected to feeder-free culture of the pluripotent stem cells. That is, according to the method, pluripotent stem cells are subjected to maintenance culture while conditioning the serum-free medium with feeder cells, and the cultured pluripotent stem cells are then subjected to feeder-free culture. According to this method, the growth capacity of the pluripotent stem cells in feeder-free culture can further be enhanced.

The pluripotent stem cells, feeder cells, culture conditions, procedures, and other conditions to be employed in this method are the same as those described above. A serum-free medium similar to that described above for the use in the preparation of the conditioned medium is preferably used.

In one embodiment, pluripotent stem cells can be grown with high efficiency by culturing pluripotent stem cells on feeder cells using a serum-free medium containing L-ascorbic acid, insulin, transferrin, selenium, and sodium bicarbonate and containing none of arginine, serum, and serum replacement, and then carrying out feeder-free culture of the cultured pluripotent stem cells. According to this method, feeder-free culture can be particularly preferably carried out using, for example, a macromolecular compound such as Matrigel® or a synthetic polymer, a culture substrate. An example of the synthetic polymer is hydrogel, such as temperature-sensitive hydrogel comprising 2-(diethylamino)ethyl acrylate as a backbone. For example, feeder-free culture can be carried out with the use of a culture vessel, such as a culture dish, the inside of which is coated with the culture substrate. The pluripotent stem cells are cultured on feeder cells, the feeder cells are removed therefrom, and the pluripotent stem cells are transferred to and cultured in a medium in a culture vessel that does not contain feeder cells. Thus, feeder-free culture can be preferably carried out.

In this method, feeder-free culture can be carried out using a conditioned medium prepared from a serum-free medium that contains L-ascorbic acid, insulin, transferrin, selenium, and sodium bicarbonate and does not contain a serum nor serum replacement. Alternatively, the feeder-free culture may be carried out using any other serum-free medium instead of a conditioned medium. According to this method, the growth (i.e., undifferentiated growth) of pluripotent stem cells in feeder-free culture can be remarkably enhanced even in the latter alternative case.

EXAMPLES

Hereafter, the present invention is described in more detail with reference to the examples, although the technical scope of the present invention is not limited to these examples.

Example 1

In this Example, undifferentiated human iPS cells that had been subjected to maintenance culture on mouse embryonic fibroblasts (MEFs; feeder cells) inactivated via mitomycin treatment were transferred into a well of a culture dish coated with vitronectin (VTN-N), in the absence of feeder cells, and then cultured in a MEF-conditioned nutrient medium, as described below.

1. Preparation of Human iPS Cells

201B7 cell line from iPS Academia Japan, Inc. (Kyoto, Japan) (Takahashi K., et al., Cell 131, 1-12, 2007) was used as human iPS cells (undifferentiated human iPS cells). The human iPS cells were subjected to maintenance culture on a plastic culture dish in which mouse embryonic fibroblasts (MEFs; feeder cells) inactivated via mitomycin treatment had been seeded. Culture was conducted using a medium prepared by supplementing DMEM/F12 medium (Dulbecco's Modified Eagle's Medium/Nutrient Mixture F-12 Ham; Sigma D6421) with KNOCKOUT™ SR (KnockOut™ Serum Replacement or KSR; Gibco) at a final concentration of 20%, 0.1 mM NEAA (non-essential amino acids), 2 mM L-glutamine, 5 ng/ml human FGF2 (referred to as "basic FGF" or "bFGF"), and 0.1 mM 2-mercaptoethanol, in a $CO_2$ incubator at 37° C. and 5% $CO_2$. Passaging was conducted every 6 or 7 days. During passaging, human iPS cell colonies were detached from a feeder cell layer using a detaching solution (a collagenase solution), and small masses of about 20 to 50 cells were formed via pipetting and then seeded on a fresh feeder cell layer.

The human iPS cells that had been subjected to maintenance culture on feeder cells as described above were detached with a detaching solution, small masses of about 20 to 50 cells were formed via pipetting, and centrifugation was conducted at 300 rpm for 5 minutes to recover iPS cells. The recovered iPS cells were incubated on a gelatin-coated culture dish for 30 minutes, thereby allowing MEFs to adhere to the dish, and iPS cells suspended in the medium were collected, so as to remove MEFs. Subsequently, the recovered iPS cells were divided into 4 fractions (¼ aliquots), and the cells were seeded in a plastic culture dish coated with vitronectin (VTN-N; Gibco). The coating of the culture dish with vitronectin (VTN-N) was conducted via incubation with a vitronectin solution at 0.5 μg/cm² at room temperature for 1 hour.

2. Preparation of Conditioned Medium

A conditioned medium (CM) was prepared from a serum-free medium using mouse embryonic fibroblasts (MEFs) inactivated via mitomycin treatment. The mouse embryonic fibroblasts (MEFs) inactivated via mitomycin treatment were seeded in a medium for MEF (DMEM medium supplemented with 10% FBS) at a cell density of about 500,000 cells per 60-mm dish. After the cells were cultured for at least 16 hours, the cells were washed with PBS(−) and then with a serum-free medium, and the medium was exchanged with a fresh portion of the same serum-free medium. The composition of the serum-free medium used is as follows.

Serum-free medium A (DMEM/F12 medium, 64 mg/L ascorbyl-2-phosphate magnesium, and 543 mg/L sodium bicarbonate)

Serum-free medium A+ITS (DMEM/F12 medium, 64 mg/L ascorbyl-2-phosphate magnesium, 543 mg/L sodium bicarbonate, 1% ITS (insulin-transferrin-selenium; Life Technologies))

The serum-free medium was supplemented with 100 μg/L human FGF2 and 2 μg/L TGF-β1 as growth factors before conditioning (supplementation with FGF+TGF). In parallel, another conditioned medium was prepared using a serum-free medium supplemented with no growth factors.

The media exchange was followed by incubation in a $CO_2$ incubator at 37° C. and 5% $CO_2$ for 24 hours.

The medium was recovered after culture for 24 hours and centrifuged at 1,000 rpm for 5 minutes, and the resulting liquid medium (supernatant) was used as an MEF-conditioned medium.

3. iPS Cell Culture without Feeder Cells 2 ml of the MEF-conditioned medium prepared in Section 2 of this Example was added to the iPS cells seeded in the culture dish coated with vitronectin (VTN-N) in Section 1 of this Example. At this phase, 100 μg/L human FGF2 and 2 μg/L TGF-β1 were added to the MEF-conditioned medium that had been prepared without the addition of human FGF2 or 2 μg/L TGF-β1 as growth factors. The iPS cells were cultured in the MEF-conditioned medium at 37° C. and 5% $CO_2$ for 5 days.

The cultured cells were stained with alkaline phosphatase. The staining was carried out by fixing the cells on a culture plate with 10% formalin, adding 1 ml of One-step NBT/BCIP solution (Pierce) thereto, and allowing it to stand at room temperature under light-shielded conditions for 30 minutes.

As shown in FIG. 1, the MEF-conditioned medium prepared with a serum-free medium A+ITS provides a high growth capacity of iPS cells (FIGS. 1A and C). While iPS cells exhibited a good growth capacity when growth factors were added after conditioning (FIG. 1C), the iPS cell growth capacity was further improved when using a conditioned medium prepared with a medium supplemented with growth factors (FIG. 1A).

Comparative Example 1 iPS cells were cultured with a serum-free conditioned medium as described in Example 1, except that the MEF-conditioned medium was prepared using serum-free medium A (DMEM/F12, 64 mg/L ascorbyl-2-phosphate magnesium, and 543 mg/L sodium bicarbonate) as a serum-free medium, and without the addition of growth factors, and then 1% ITS (insulin-transferrin-selenium), 100 μg/L human FGF2, and 2 μg/L TGF-β1 were added thereto during addition of the medium to iPS cells for culture.

FIG. 1D shows the results of observation after alkaline phosphatase staining. In the MEF-conditioned medium prepared using serum-free medium A containing neither ITS nor growth factors, almost no growth of iPS cells was observed even if ITS, human FGF2, and TGF-β1 were added during iPS cell culture.

Comparative Example 2 iPS cells were prepared as described in Example 1. Serum-free medium A+ITS (DMEM/F12, 64 mg/L ascorbyl-2-phosphate magnesium, 543 mg/L sodium bicarbonate, 1% ITS (insulin-transferrin-selenium; Life Technologies)) was added without conditioning of the medium with MEF to the iPS cells seeded in a culture dish coated with vitronectin (VTN-N). In addition, 100 µg/L human FGF2 and 2 µg/L TGF-β1 were added thereto, and iPS cells were cultured as described in Example 1.

FIG. 1B shows the results of observation after alkaline phosphatase staining. When iPS cells were cultured using the serum-free medium A+ITS which was not conditioned with MEF, the iPS cell growth capacity remained low even when growth factors were added.

Comparative Example 3 iPS cells were cultured in a serum-free conditioned medium as described in Example 1, except that serum-free medium B+ITS (DMEM (Dulbecco's Modified Eagle's Medium), 2 mM L-glutamine, 0.1 mM NEAA (non-essential amino acids), 1% ITS (insulin-transferrin-selenium), 0.1 mM β-mercaptoethanol) was used as a serum-free medium and 100 µg/L human FGF2 and 2 µg/L TGF-β1 were added as growth factors (supplementation with FGF+TGF) for conditioning. In addition, as another experiment, iPS cells were cultured using the serum-free medium B+ITS which was not conditioned with MEF, and with the addition of 100 µg/L human FGF2 and 2 µg/L TGF-β1 as with Comparative Example 2.

FIG. 1 shows the results of observation after alkaline phosphatase staining. iPS cell growth was not observed in the MEF-conditioned medium prepared using serum-free medium B+ITS (FIG. 1E) nor in the serum-free medium B+ITS which was not conditioned with MEF (FIG. 1F), regardless of the presence or absence of conditioning with MEFs. The results show that growth-promoting factors for iPS cells are not secreted into a conditioned medium prepared with serum-free medium B+ITS, unlike a conditioned medium prepared using serum-free medium A+ITS.

Example 2

In this Example, undifferentiated human iPS cells that had been subjected to maintenance culture on mouse embryonic fibroblasts (MEFs; feeder cells) inactivated via mitomycin treatment were transferred into a well of a culture dish coated with Matrigel, vitronectin (VTN-N), or PCM-DM, in the absence of feeder cells, and then cultured in a MEF-conditioned nutrient medium, as described below. PCM-DM is an extracellular (pericellular) matrix of human decidua-derived mesenchymal cells (D. Kanematsu et al., Differentiation, 82, 77-88, 2011).

1. Preparation of Human iPS Cells

201B7 cell line from iPS Academia Japan, Inc. was used as human iPS cells (undifferentiated human iPS cells). The human iPS cells were subjected to maintenance culture on a plastic culture dish in which mouse embryonic fibroblasts (MEFs; feeder cells) inactivated via mitomycin treatment had been seeded. Culture was conducted using a medium prepared by supplementing DMEM/F12 medium (Dulbecco's Modified Eagle's Medium/Nutrient Mixture F-12 Ham; Sigma D6421) with KNOCKOUT™ SR (KnockOut™ Serum Replacement or KSR; Gibco) at a final concentration of 20%, 0.1 mM NEAA (non-essential amino acids), 2 mM L-glutamine, 5 ng/ml human FGF2 (referred to as "bFGF" or "FGF2"), and 0.1 mM 2-mercaptoethanol, in a $CO_2$ incubator at 37° C. and 5% $CO_2$. Passaging was conducted every 6 or 7 days. During subculture, human iPS cell colonies were detached from a feeder cell layer using a detaching solution (a collagenase solution), and small masses of about 20 to 50 cells were formed via pipetting and then seeded on a fresh feeder cell layer.

The human iPS cells that had been subjected to maintenance culture on feeder cells as described above were detached with a detaching solution, small masses of about 20 to 50 cells were formed via pipetting, and centrifugation was conducted at 300 rpm for 5 minutes to recover iPS cells. The recovered iPS cells were incubated on a gelatin-coated culture dish for 30 minutes, thereby allowing MEFs to adhere to the dish, and iPS cells suspended in the medium were collected, so as to remove MEFs.

2. Preparation of Conditioned Medium

A conditioned medium (CM) was prepared from a serum-free medium using mouse embryonic fibroblasts (MEFs) inactivated via mitomycin treatment. The mouse embryonic fibroblasts (MEFs) inactivated via mitomycin treatment were seeded in a medium for MEF (DMEM medium supplemented with 10% FBS) at a cell density of about 500,000 cells per 60-mm dish. After the cells were cultured for at least 16 hours, the cells were washed with PBS(−) and then with serum-free medium A (DMEM/F12 medium, 64 mg/L ascorbyl-2-phosphate magnesium, and 543 mg/L sodium bicarbonate; which is also referred to as "basal medium A") supplemented with 1% ITS, 100 µg/L human FGF2, and 2 µg/L TGF-β1, and the medium was exchanged with a fresh portion of the same serum-free medium.

The media exchange was followed by incubation in a $CO_2$ incubator at 37° C. and 5% $CO_2$ for 24 hours. The medium was recovered after culture for 24 hours and exchanged with a fresh medium up to 6 times repeatedly. The recovered medium was centrifuged at 1,000 rpm for 5 minutes, and the resulting liquid medium was used as a MEF-conditioned medium (serum-free medium A+ITS+FGF+TGF).

3. Preparation of Substrate-Coated Culture Dish

The coating of culture dish with Matrigel was conducted in accordance with the instructions provided by Life Technologies via incubation with a 30-fold dilution of Matrigel® (BD) in DMEM/F12 at room temperature for 1 hour.

The PCM-DM-coated culture dish was prepared in accordance with a conventional method (D. Kanematsu et al., Differentiation, 82, 77-88, 2011). Specifically, first, human decidua-derived mesenchymal cells were seeded in a plastic culture dish coated with 0.1% gelatin at $3.5 \times 10^4$ cells/cm$^2$, and cultured for 3 days while maintaining confluence. The cultured cells were washed with PBS(−), and then the washed cells were treated with deoxycholic acid (treatment at 4° C. for 30 minutes with the addition of 0.5% sodium deoxycholate/10 mM Tris-HCl (pH 8.0) to the culture dish) to lyse the cell components. Thereafter, extracellular matrix components left on the culture dish were washed with PBS(−).

The vitronectin (VTN-N)-coated culture dish was prepared in the same manner as in Example 1.

4. iPS Cell Culture without Feeder Cells

The iPS cells prepared, recovered and subjected to the removal of MEFs in Section 1 of this Example were divided into 4 fractions (¼ aliquots) and seeded in a plastic culture dish coated with Matrigel, vitronectin, or PCM-DM prepared in Section 3 of this Example. The MEF-conditioned medium from serum-free medium A+ITS+FGF+TGF, prepared in Section 2 of this Example, was used to conduct culture at 5% $CO_2$ and 37° C. for 5 days.

In parallel, the iPS cells prepared, recovered and subjected to the removal of MEFs in Section 1 of this Example were cultured in the same medium except for not being conditioned with MEF.

Figure 2:
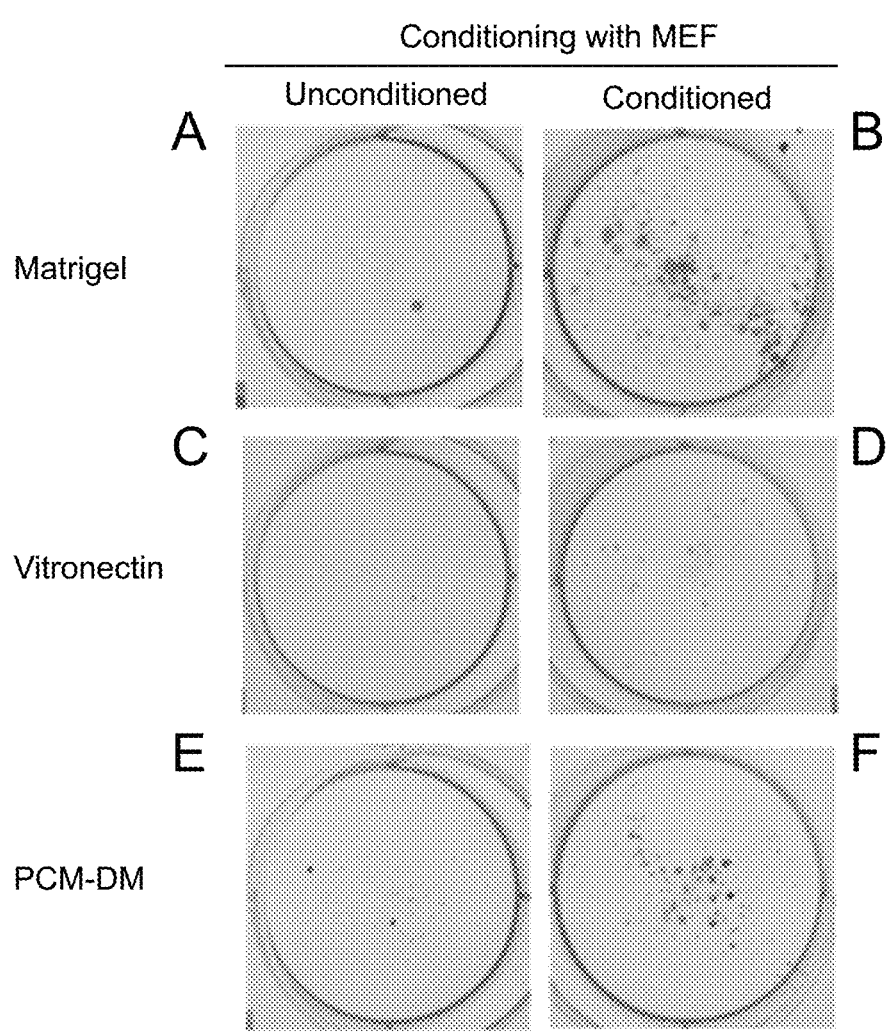
FIG. 2 presents photographs showing the results of the growth of human iPS cells in serum-free conditioned medium in a plastic culture dish coated with various culture substrates. As a culture substrate, Matrigel® (see, FIG. 2A, B), vitronectin (see, FIGS. 2C, D), and PCM-DM (see, FIGS. 2E, F) were used. In A, C, and E, an unconditioned serum-free medium is used. In B, D, and F, an MEF-conditioned medium is used.

FIG. 2 shows the results of observation after alkaline phosphatase staining. When culture was conducted using the MEF-conditioned medium, the iPS cell growth capacity was enhanced in the culture dishes coated with any of the culture substrates (i.e., Matrigel, vitronectin, and PCM-DM).

Example 3

Culture of iPS cells in the MEF-conditioned medium (serum-free medium A+ITS+FGF+TGF) and in the medium (serum-free medium A+ITS+FGF+TGF) that was not conditioned with MEF using the Matrigel- or PCM-DM-coated plastic culture dishes in accordance with Example 2 was continued for five passages. FIG. 3 shows the results of comparison of cell growth rates during such culture. When iPS cells were cultured with the use of the MEF-conditioned medium from serum-free medium A+ITS+FGF+TGF, the growth efficiency was approximately 300 times greater than that attained with the use of the unconditioned medium.

Example 4

Culture of iPS cells in the MEF-conditioned medium (serum-free medium A+ITS+FGF+TGF) and in the medium (serum-free medium A+ITS+FGF+TGF) that was not conditioned with MEF using the vitronectin-coated plastic culture dishes in accordance with Example 2 was continued for four passages. As controls, iPS cells were cultured using MEFs as feeder cells (on-feeder culture), and iPS cells were cultured in MEF-CM. The control MEF-CM was prepared by supplementing DMEM/F12 medium (Dulbecco's Modified Eagle's Medium/Nutrient Mixture F-12 Ham; Sigma D6421) with KNOCKOUT™ SR (KnockOut™ Serum Replacement or KSR; Gibco) at final concentration of 20% to prepare a medium, culturing MEFs in the resulting medium at 37° C. and 5% $CO_2$, and recovering the medium.

As a result of alkaline phosphatase staining, the iPS cells were found to be alkaline phosphatase (ALP)-positive and thus maintain the undifferentiated state during culture in any of the culture conditions.

Figure 4:
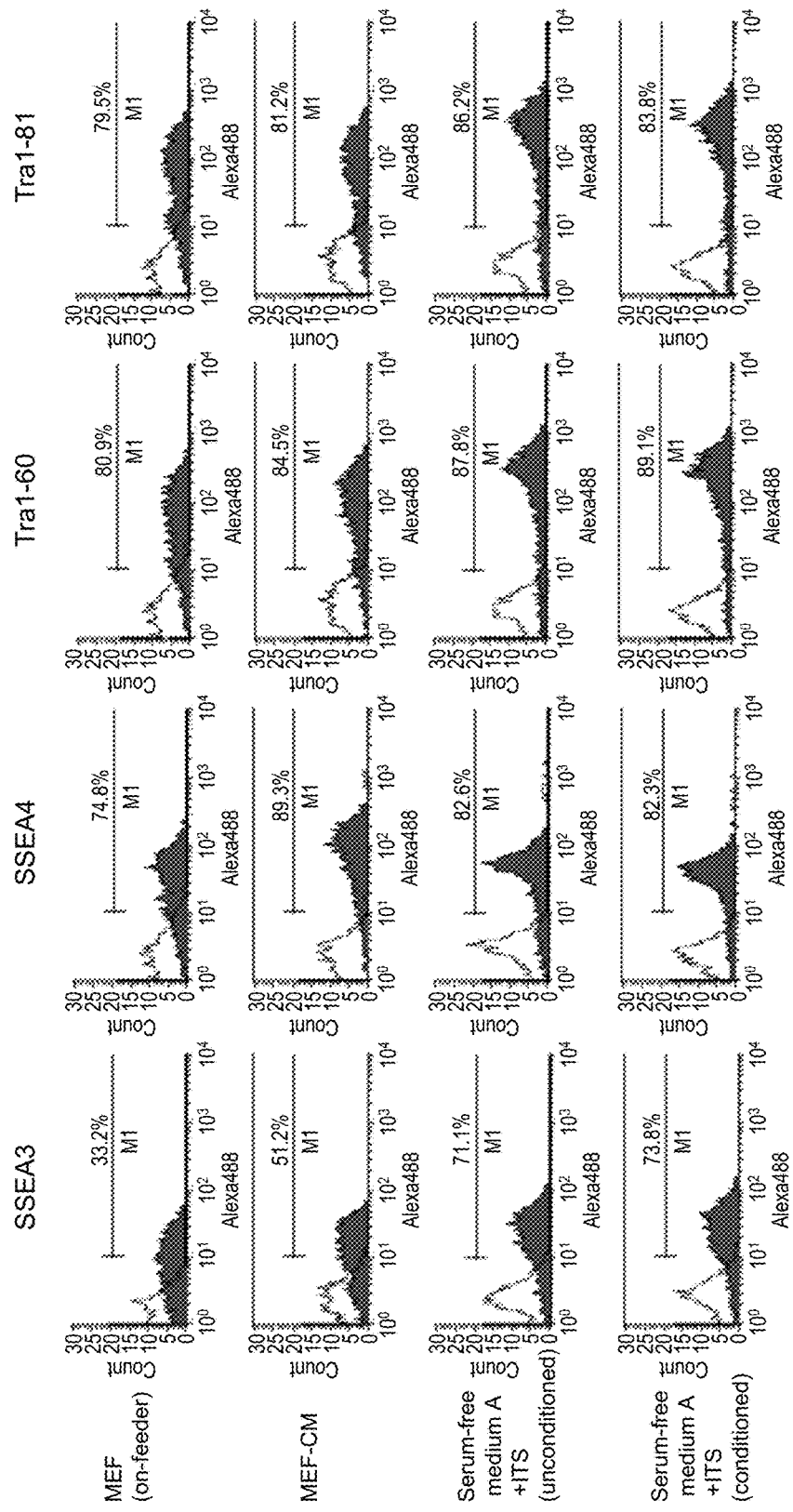
FIG. 4 shows the results of expression analysis of undifferentiation markers via flow cytometry for human iPS cells cultured in MEF-conditioned serum-free medium or unconditioned serum-free medium.

The iPS cells after culture were subjected to flow cytometry analysis. As a result, the iPS cells were found to be positive for undifferentiation markers SSEA3, SSEA4, Tra1-60, and Tra1-81 (FIG. 4). This indicates that the expression status of undifferentiation markers on iPS cells cultured in the conditioned serum-free medium exhibiting an enhanced growth capacity as described above in the Examples does not differ from that in the case of culture in the unconditioned serum-free medium, on-feeder culture, or culture in MEF-CM. Accordingly, no change was observed in cell traits even in the conditioned serum-free medium.

Further, RT-qPCR analysis was conducted and expressions of undifferentiation marker genes Oct4, NANOG, and SOX2 were also observed.

Thus, it was shown that culture in an MEF-conditioned serum-free medium is capable of enhancing the growth efficiency of iPS cells while maintaining the undifferentiated state.

Example 5

Proteins secreted in the conditioned medium prepared in Example 1 from the medium supplemented with ITS and growth factors (FIG. 1A) and in the conditioned medium prepared in Comparative Example 1 from the medium containing neither ITS nor growth factors (FIG. 1D) were analyzed via two-dimensional gel electrophoresis with reference to the unconditioned medium as a control. First, proteins were recovered from 1 ml of each medium via acetone precipitation. The recovered proteins were suspended in swelling buffer, added to the immobilized pH gradient gel, Ready Strip IPG strip (pH 3-10, 11 cm; Bio-Rad), and allowed to swell for 12 hours and then subjected to isoelectric focusing electrophoresis in an isoelectric focusing apparatus, Protean® IEF cell (Bio-Rad) at 50 V and 20° C. Thereafter, the ReadyStrip IPG strip was shaken in an SDS-PAGE-equilibrated buffer (containing 2% DTT) for 10 minutes and then in an SDS-PAGE-equilibrated buffer (containing 2.5% iodoacetamide) for 10 minutes. Proteins were then developed via SDS-PAGE. In the conditioned medium prepared in Example 1 from the medium supplemented with ITS and growth factors and in the conditioned medium prepared in Comparative Example 1 from the medium containing neither ITS nor growth factors, 40 and 12 spots of MEF-derived secretory proteins were detected, respectively. This indicates that the conditioned medium prepared in Example 1 from the medium supplemented with ITS and growth factors (FIG. 1A) contains proteins that contribute to promotion of the growth.

Example 6

1. Feeder-Free Culture Using MEF-Conditioned Medium

In accordance with the section entitled "1. Preparation of human iPS cells" in Example 2, human iPS cells were cultured on mouse embryonic fibroblasts (MEFs; feeder cells) inactivated via mitomycin treatment (i.e., on-feeder culture), the cells were recovered, and MEFs were then removed therefrom.

The human iPS cells thus prepared were transferred into a well of a Matrigel-coated culture dish in the absence of feeder cells, and then cultured using various media (feeder-free culture). The following media were used.

Figure 5:
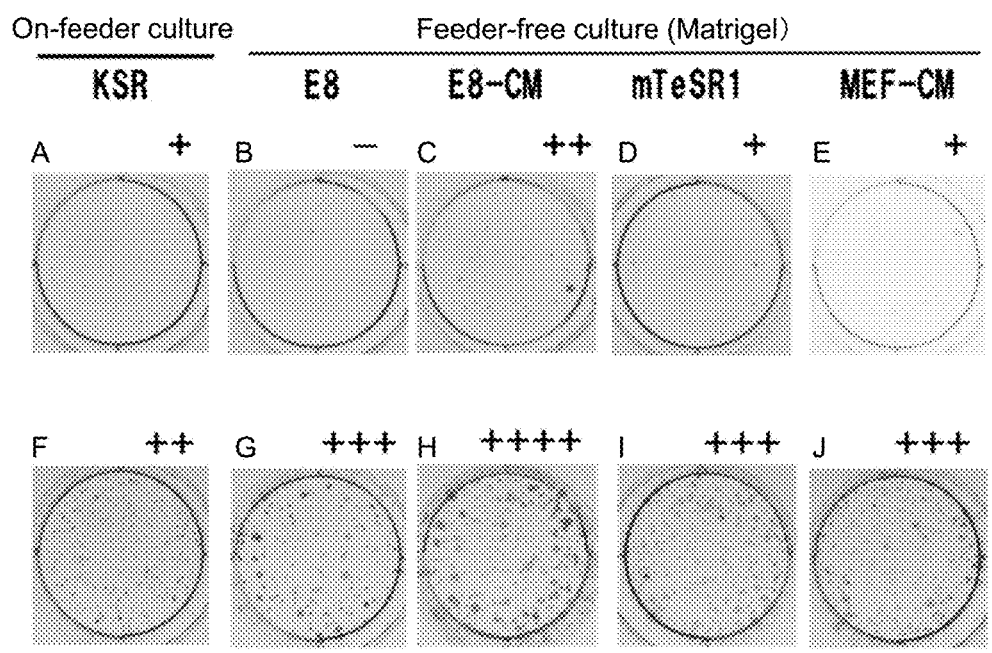
FIGS. 5A-5J present photographs showing the results of comparison of the growth capacity of human iPS cells between before and after transfer from on-feeder culture with the use of serum-replacement-containing media (FIGS. 5B to 5E) or serum-free media containing given components (FIGS. 5G to 5J) to feeder-free culture.

Serum-free medium A+ITS+FGF+TGF (DMEM, 2 mM L-glutamine, 0.1 mM NEAA, 1% ITS, and 0.1 mM β-mercaptoethanol, supplemented with 100 µg/L human FGF2 and 2 µg/L TGF-β1) (E8 in FIG. 5)

MEF-conditioned medium from serum-free medium A+ITS+FGF+TGF, prepared in accordance with the section entitled "2. Preparation of conditioned medium" in Example 2 (E8-CM in FIG. 5)

MEF-CM prepared in accordance with Example 4 mTeSR™ 1 medium (modified Tenneille Serum Replacer 1) (STEMCELL Technologies)

As a control, a medium was prepared by the addition of KNOCKOUT™ SR at final concentration of 20%, 0.1 mM NEAA, 2 mM L-glutamine, 5 ng/ml human FGF2, and 0.1 mM 2-mercaptoethanol to DMEM/F12 medium and another experiment was carried out by performing on-feeder culture in the prepared medium (KSR in FIG. 5). Coating of the culture dish with Matrigel was conducted in accordance with the section entitled "3. Preparation of substrate-coated culture dish" in Example 2.

Culture and alkaline phosphatase staining were carried out in accordance with the procedures described in the section entitled "4. iPS cell culture without feeder cells" in Example 2, except that the duration of culture was 4 days.

The results are shown in FIG. 5A to E. After the transition from on-feeder culture to feeder-free culture, the growth was observed in the MEF-conditioned medium (E8-CM) from serum-free medium A+ITS+FGF+TGF, while almost no growth was observed in other media.

2. Feeder-Free Culture after Transfer from On-Feeder Culture in a Medium Containing Given Components Human iPS cells were cultured on mouse embryonic fibroblasts (MEFs; feeder cells) inactivated via mitomycin treatment (i.e., on-feeder culture), recovered, and subjected to the removal of MEFs, in accordance with the section entitled "1. Preparation of human iPS cells" in Example 2, except for the use of, as a medium, the serum-free medium A+ITS+FGF+TGF instead of the medium prepared with the addition of KNOCKOUT™ SR at final concentration of 20%, 0.1 mM NEAA, 2 mM L-glutamine, 5 ng/ml human FGF2, and 0.1 mM 2-mercaptoethanol to DMEM/F12 medium.

The human iPS cells thus prepared were transferred into a well of a Matrigel-coated culture dish in the absence of feeder cells, and the cells were then subjected to feeder-free culture using various media as used in Section 1 of this Example, followed by alkaline phosphatase staining, in the section.

As a result, remarkably higher growth capacities were observed in feeder-free culture with any of the media, compared with the results shown in Section 1 of this Example.

This shows that the growth capacity of pluripotent stem cells can further be enhanced by conducting on-feeder culture with the use of the above-mentioned serum-free medium, followed by transfer therefrom to feeder-free culture.

Example 7

A culture dish coated with temperature-sensitive hydrogel comprising 2-(diethylamino)ethyl acrylate as a backbone was prepared (Zhang et al., Nature Communications, (2013) 4, Article number: 1335). Specifically, a mixture of N-acryloyl-N'-propylpiperazine, 2,2'-(ethylenedioxy)bis(ethylamine)monoacrylamide, a crosslinking agent, and a photopolymerization initiator in N-methyl-2-pyrrolidone was added to a plastic culture dish that had been treated with 3-(trimethoxysilyl)propyl methacrylate in advance, UV light at 365 nm was applied thereto for 30 minutes, and the dish was allowed to stand at 50° C. overnight. Thereafter, the dish was successively washed with ethanol and then acetone, followed by air drying.

With the use of the hydrogel-coated culture dish thus prepared instead of the Matrigel-coated culture dish, human iPS cells were subjected to on-feeder culture and then feeder-free culture using various media in accordance with Section 2 of Example 6. As a result, iPS cells were found to exhibit a high growth capacity in any media.

INDUSTRIAL APPLICABILITY

The present invention can be suitably used for feeder-free, serum-free culture of pluripotent stem cells. In addition, the present invention can be used for preparation of a serum-free medium for culture of human pluripotent stem cells comprising growth-promoting factors that facilitate pluripotent stem cell growth with high safety, such as a serum-free, complete synthetic medium. With the use of such medium, feeder-free culture of human pluripotent stem cells can be carried out stably with high efficiency. According to the present invention, also, a medium that enables isolation of growth-promoting factors secreted from feeder cells, such as MEFs, can be obtained. Such medium can be used for screening for factors useful for human pluripotent stem cell growth.

All publications, patents, and patent applications cited herein are incorporated herein by reference in their entirety.

The invention claimed is:

1. A method for growing pluripotent stem cells comprising carrying out feeder-free culture of pluripotent stem cells in a conditioned medium which is generated by culturing feeder cells in a serum-free medium that contains L-ascorbic acid, insulin, transferrin, selenium, and sodium bicarbonate and does not contain a serum nor serum replacement.

2. The method according to claim 1, wherein the serum-free medium is DMEM/F12 medium containing L-ascorbic acid, insulin, transferrin, selenium, and sodium bicarbonate.

3. The method according to claim 1, wherein the culturing of the feeder cells is carried out with the addition of growth factors to the serum-free medium.

4. The method according to claim 1, wherein the culturing of the feeder cells is carried out without the addition of growth factors to the serum-free medium and the feeder-free culture of pluripotent stem cells is carried out with the addition of a growth factor to the conditioned medium.

5. The method according to claim 2, wherein the culturing of the feeder cells is carried out with the addition of growth factors to the serum-free medium.

6. The method according to claim 2, wherein the culturing of the feeder cells is carried out without the addition of growth factors to the serum-free medium and the feeder-free culture of pluripotent stem cells is carried out with the addition of a growth factor to the conditioned medium.

7. The method according to claim 3, wherein the growth factor is FGF2 and/or TGF-β1.

8. The method according to claim 5, wherein the growth factor is FGF2 and/or TGF-β1.

9. The method according to claim 1, wherein the feeder cells are mouse embryonic fibroblasts.

10. The method according to claim 1, wherein the pluripotent stem cells are ES cells or iPS cells.

* * * * *